United States Patent

Rittner et al.

[11] Patent Number: 5,808,142

[45] Date of Patent: Sep. 15, 1998

[54] PROCESS FOR THE PREPARATION OF 2-HYDROXYNAPHTHALENE-6-CARBOXYLIC ACID

[75] Inventors: Siegbert Rittner, Mörfelden; Hans-Martin Rüffer, Hofheim; Jörg Schmid, Eppstein; Thomas Wisser, Limburg, all of Germany

[73] Assignee: Hoechst Aktiengesellschaft, Frankfurt, Germany

[21] Appl. No.: 305,406

[22] Filed: Sep. 13, 1994

Related U.S. Application Data

[63] Continuation of Ser. No. 245,961, May 19, 1994, abandoned.

[30] Foreign Application Priority Data

May 21, 1993 [DE] Germany .......................... 43 16 932.5

[51] Int. Cl.$^6$ .................................................. C07C 51/10
[52] U.S. Cl. ......................................... 562/406; 562/467
[58] Field of Search ..................................... 562/406, 467

[56] References Cited

U.S. PATENT DOCUMENTS

| | | | |
|---|---|---|---|
| 3,655,744 | 4/1972 | Yatsuhara et al. . | |
| 3,718,690 | 2/1973 | Bushiere et al. | 562/406 |
| 4,239,913 | 12/1980 | Ueno et al. | 562/425 |
| 4,329,494 | 5/1982 | Montgomery . | |
| 4,345,094 | 8/1982 | Mueller et al. . | |
| 4,374,262 | 2/1983 | McGinnis | 562/406 |
| 4,393,191 | 7/1983 | East . | |
| 5,011,984 | 4/1991 | Ueno et al. . | |

FOREIGN PATENT DOCUMENTS

| | | |
|---|---|---|
| 0 254 596 | 1/1988 | European Pat. Off. . |
| 955 598 | 12/1956 | Germany . |
| 1493358 | 2/1965 | Germany . |
| 28 37 053 | 4/1979 | Germany . |
| 1155776 | of 0000 | United Kingdom . |
| 815835 | 7/1959 | United Kingdom . |
| WO 91/11422 | 8/1991 | WIPO . |

*Primary Examiner*—Paul J. Killos
*Attorney, Agent, or Firm*—Frommer Lawrence & Haug LLP

[57] ABSTRACT

A process for the preparation of 2-hydroxynaphthalene-6-carboxylic acid using potassium carbonate and CO at temperatures above 260° C. and at a pressure of at least 10 bar comprises using 2-hydroxynaphthalene-3-carboxylic acid and/or 2-hydroxynaphthalene-3,6-dicarboxylic acid and/or their potassium salts and, if desired, potassium β-naphtholate as starting materials.

The process according to the invention enables a considerable increase, by reusing the secondary products, in the product selectivity with regard to 2-hydroxy-naphthalene-6-carboxylic acid.

4 Claims, No Drawings

_PROCESS FOR THE PREPARATION OF 2-HYDROXYNAPHTHALENE-6-CARBOXYLIC ACID_

This application is a continuation of application Ser. No. 08/245,961, filed May 19, 1994 now abandoned.

The invention relates to a process for the preparation of 2-hydroxynaphthalone-6-carboxylic acid or its di-salt by reacting an alkali metal β-naphtholate with carbon monoxide and an alkali metal carbonate.

2-Hydroxynaphthalene-6-carboxylic acid is an important intermediate, for example in the production of dyes, polyesters, pharmaceuticals and textile assistants (see for example EP-A 0 292 955 and U.S. Pat. No. 4,393,191).

In industry, this compound is prepared by the Kolbe-Schmitt reaction, i.e. by reacting the corresponding β-naphtholate with carbon dioxide (see e.g. EP-A 0 254 596 or U.S. Pat. No. 5,011,984). However, there is still room for improvement in the yields of this process.

An alternative process for preparing aromatic hydroxy carboxylic acids is described, inter alia, in GB 1 155 776 (= U.S. Pat. No. 3,655,744). In this process specific aromatic alkali metal naphtholates or alkaline earth metal naphtholates are reacted with alkali metal or alkaline earth metal carbonates, carboxylates or di-carboxylates in the presence of carbon monoxide. The yields, and in particular the product selectivity, of the process described therein are, however, not adequate for all areas.

WO 91/11422 describes a process for the preparation of 2-hydroxynaphthalone-6-carboxylic acid from potassium β-naphtholate, potassium carbonate and CO, this reaction being carried out in a potassium formate melt.

Although this process, in contrast to that described in GB 1 155 776, results predominantly in the desired 2-hydroxynaphthalene-6-carboxylic acid, secondary products such as 2-hydroxynaphthalene-3-carboxylic acid and 2-hydroxynaphthalene-3,6-dicarboxylic acid are also formed, and there is therefore room for further improvements.

Surprisingly it has now been found that 2-hydroxynaphthalene-6-carboxylic acid, 2-hydroxynaphthalene-3-carboxylic acid, 2-hydroxynaphthalene-3,6-dicarboxylic acid and β-naphthol and their salts can be converted into one another by reaction with CO and carbonate at elevated pressure and elevated temperature. It has been demonstrated in this context that the composition of the starting mixture has little influence on the distribution of the products.

The possibility of such a conversion with the formation of 2-hydroxynaphthalene-6-carboxylic acid has previously only been described under the conditions of the Kolbe-Schmitt reaction (see e.g. U.S. Pat. Nos. 4,345,094 and No. 4,329,494).

The invention therefore relates to a process for the preparation of 2-hydroxynaphthalene-6-carboxylic acid using potassium carbonate and CO at temperatures above 260° C. and at a pressure of at least 10 bar, which comprises using 2-hydroxynaphthalene-3-carboxylic acid and/or 2-hydroxynaphthalene-3,6-dicarboxylic acid and/or their potassium salts and, if desired, potassium β-naphtholate as starting materials.

The process according to the invention enables a considerable increase, by reusing the secondary products, in the product selectivity with regard to 2-hydroxynaphthalene-6-carboxylic acid.

The compounds employed in the process according to the invention, 2-hydroxynaphthalene-3-carboxylic acid and/or 2-hydroxynaphthalene-3, 6-dicarboxylic acid and/or their potassium salts, are advantageously derived from the production of 2-hydroxynaphthalene-6-carboxylic acids, where they occur as secondary products.

The separation of the secondary products employed according to the invention from the 2-hydroxynaphthalene-6-carboxylic acid can be carried out in a familiar manner by taking up the alkaline reaction product in water and then selectively precipitating the products using mineral acids. In accordance with the different acid strengths, the unreacted β-naphthol can be separated off at neutral pH, the 2-hydroxynaphthalene-6-carboxylic acid analogously at pH 4 and the remaining hydroxy and/or hydroxynaphthalene naphthalene dicarboxylic acids at a pH of about 1. Fine purification of the 2-hydroxynaphthalene-6-carboxylic acid is carried out according to known procedures, for example by pressurized recrystallization in water or, more advantageously, by purification using 1,4-dioxane.

The hydroxynaphthalene carboxylic acids separated off can be combined, converted into their potassium salts by reaction with KOH or $K_2CO_3$, analogously to the preparation of the potassium β-naphtholate, and dried. After making up the batch with a quantity of potassium β-naphtholate corresponding to the quantity of 2-hydroxynaphthalene-6-carboxylic acid separated off, and the small losses which are attributed to nonspecific secondary reactions (resin formation), a starting product suitable for the process according to the invention is made available.

The process according to the invention is carried out according to methods as described, for example, in WO 91/11422 and in the German patent application with the title "Verfahren zur Herstellung von aromatischen Hydroxycarbonsäuren" [Process for the preparation of aromatic hydroxy carboxylic acids] or else, in general, in GB 1,155,776. The German patent application proposes a process for the preparation of aromatic hydroxy carboxylics acids or their salts by reaction of phenolates or naphtholates with alkali metal carbonates and carbon monoxide, which comprises adding the solid starting materials—alkali metal carbonate and alkali metal phenolate or naphtholate—to the reaction in the form of a dispersion in an inert organic liquid.

The process according to the invention is carried out in the presence of CO. The CO can be present as a gas atmosphere over the reaction mixture or can be injected over or even directly into the mixture. To permit the successful progress of the reaction, at least stoichiometric quantities of CO, based on the β-naphtholate, are required.

The process according to the invention is carried out at a pressure of from 10 to 150 bar, preferably from 10 to 100 bar and particularly preferably from 10 to 30 bar, the pressure referred to being that at the reaction temperature.

Technical-grade carbon monoxide can be used, i.e. small amounts of other gases such as $N_2$, $CH_4$, $CO_2$ and $H_2$ are not critical.

The reaction temperature can be varied within broad limits, depending on the properties of the starting materials, products and solvents or dispersants. The temperatures generally employed are from 150° to 400° C., preferably from 200° to 350° C. and especially preferably from 250° to 350° C.

The duration of the reaction is preferably between 1 and 40 hours.

The process according to the invention can be carried out using various forms of apparatus; for example, the reactor used can be a pressure vessel or kneader which is fitted with a stirring element, which is efficient in terms of thorough mixing and CO gassing, and which pressure vessel or kneader is connected to a feed system for the dispersion. This dispersion can either be pumped in in cycles or injected, or metered in continuously.

The process according to the invention can be carried out batchwise, semicontinuously or continuously.

The potassium carbonate used according to the invention should preferably contain little moisture, in particular less than 0.5% by weight of water. However, a small amount of moisture is not critical.

Based on the β-naphtholate employed, at least equivalent quantities of carbonate should be employed. In general the stoichiometric ratio of β-naphtholate to carbonate is from 1:1 to 1:4, advantageously from 1:1 to 1:3 and preferably from 1:1 to 1:1.5.

The solvents and dispersants used according to the invention are substances or mixtures of substances which are inert under the reaction conditions, and are liquid and temperature stable, such as aliphatic, alicyclic or aromatic hydrocarbons derived from petroleum distillation. Of particular suitability are light oil, heavy oil, preferably kerosene, aromatic compounds and alkyl derivatives thereof, ouch as toluene, xylene, isopropyl—or diisopropylnaphthalene, biphenyl, alkylbiphenyls, triphenyl and alkyltriphenyls and aliphatic and aromatic ether compounds and alkyl derivatives thereof, such as diphenyl ether, anisole, dicyclohexyl ether, and mixtures of these. The dispersants do not interfere with the reaction and can be removed from the reactor by distillation or, following the reaction, can be separated off by allowing the reaction mixture to settle or by subjecting it to distillation. They have the advantage that, after the removal of any dissolved or entrained components such as β-naphthol or water, they can be reused for the production of fresh dispersions.

It is also possible, as described in WO 91/11422, to add to the reaction mixture potassium formate which is present, under the reaction conditions, as a nonviscous, clear melt.

The amount of potassium formate used is not critical and may be varied within wide limits. It is, however, advantageous to employ potassium formate in a relatively large quantity as a solvent (diluent), for example in from 2.5 to 18 times and preferably from 6 to 15 times the amount by weight of potassium β-naphtholate employed.

The 2-hydroxynaphthalene-6-carboxylic acid prepared according to the invention can be isolated in the manner described for the recovery of the starting materials.

The 2-hydroxynaphthalene-6-carboxylic acid prepared by the process according to the invention is an important intermediate in the production of polyesters, azo dyes and pharmaceuticals.

It is in particular not only a valuable building block in the synthesis of dyes, textile assistants and pharmaceuticals (see e.g. EP-A 0 292 955 A), but is also an important monomer in the production of liquid crystal polymers having outstanding properties (see e.g. U.S. Pat. No. 4,393,191).

The examples which follow illustrate the invention described above. Parts and percentages are by weight unless otherwise specified. The relationship between parts by weight and parts by volume is that of the kilogram to the liter.

EXAMPLES

Example 1

1 part of 2-hydroxynaphthalene-3-carboxylic acid together with 0.60 part of 50% strength aqueous potassium hydroxide solution are suspended in 2 parts of toluene, with stirring and heating, in a pressurized apparatus having a distillation bridge and an azeotropic-separation system. The water is distilled off to complete dryness, and the dipotassium salt of the 2-hydroxynaphthalene-3-carboxylic acid is isolated.

14 parts of the dipotassium salt of 2-hydroxynaphthalone-3-carboxylic acid are placed together with 7.4 parts of potassium carbonate and 75 parts of potassium formate in a pressure reactor and freed from residual moisture at 230° C. 95 bar of carbon monoxide are then injected, and the mixture is maintained with stirring at 280° C. for 4 hours.

The reaction mixture is cooled, taken up in water, and worked up by selective acidification in a conventional manner. The yields (based on the 2-hydroxynaphthalene-3-carboxylic acid employed) are: 47% of 2-hydroxynaphthalene-6-carboxylic acid, 7.2% of unreacted 2-hydroxynaphthalene-3-carboxylic acid, 18% of β-naphthol and 17% of 2-hydroxynaphthalene-3,6-dicarboxylic acid.

Example 2

The tripotassium salt of 2-hydroxynaphthalone-3,6-dicarboxylic acid is prepared in analogy to Example 1. It is reacted analogously to Example 1 for 5 hours using, instead of the 14 parts of 2-hydroxynaphthalone-3-carboxylic acid, 18 parts of the tripotassium salt of 2-hydroxynaphthalone-3,6-dicarboxylic acid. The yields, based on starting material, are: 41% of 2-hydroxynaphthalene-6-carboxylic acid, 7.1% of 2-hydroxynaphthalene-3-carboxylic acid, 11% of β-naphthol and 28% of 2-hydroxynaphthalene-3,6-dicarboxylic acid.

Example 3

A 3 l stainless steel autoclave is charged with 100 parts of potassium formate, and the melt is freed from residual moisture at 230° C., with stirring and in vacuo. The mixture is then heated to 280° C., and 50 bar of carbon monoxide are injected. Using a metering pump, a mixture of 120 parts of potassium β-naphtholate and 10 parts of the dipotassium salt of 2-hydroxynaphthalene-3-carboxylic acid together with 25 parts of potassium carbonate is metered in as a suspension in kerosene over the course of 5 hours. The reaction mixture is worked up to give 2-hydroxynaphthalone-6-carboxylic acid in a yield of 68%, based on the naphthol components employed. Secondary products are 10% of unreacted β-naphthol, 4% of 2-hydroxynaphthalene-3-carboxylic acid and 12% of 2-hydroxynaphthalone-3,6-dicarboxylic acid.

We claim:

1. A process for the preparation of 2-hydroxynaphthalene-6-carboxylic acid using potassium carbonate and CO at temperatures above 260° C. and at a pressure of at least 10 bar, which comprises using 2-hydroxynaphthalene-3-carboxylic acid or 2-hydroxynaphthalene-3,6-dicarboxylic acid or their potassium salts as starting materials.

2. The process as claimed in claim 1, wherein the naphthalenecarboxylic acids employed can be obtained as secondary products from the preparation of 2-hydroxynaphthalene-6-carboxylic acid.

3. The process as claimed in claim 1, wherein the naphthalenecarboxylic acids employed can be obtained as secondary products from the preparation of 2-hydroxynaphthalene-3-carboxylic acid.

4. The process as claimed in claim 1, which further comprises potassium-β-naphtholate as a starting material.

* * * * *